United States Patent [19]

Murata

[11] Patent Number: 4,562,045
[45] Date of Patent: * Dec. 31, 1985

[54] CARRIER FOR HOLDING ANALYTICAL SAMPLES

[75] Inventor: Michihiro Murata, Kyoto, Japan

[73] Assignee: Murata Manufacturing Co., Kyoto, Japan

[*] Notice: The portion of the term of this patent subsequent to Sep. 20, 2000 has been disclaimed.

[21] Appl. No.: 469,394

[22] Filed: Feb. 24, 1983

Related U.S. Application Data

[63] Continuation-in-part of Ser. No. 309,473, Oct. 7, 1981, Pat. No. 4,405,560.

[51] Int. Cl.$^4$ .......................... B01L 3/00; G01N 1/28
[52] U.S. Cl. ..................................... 422/102; 422/58; 422/68; 435/805; 436/172
[58] Field of Search .................. 422/56, 58, 66, 68, 422/102, 104; 436/44, 172; 435/805, 299, 300, 301; 356/244, 246; 250/272; 378/79

[56] References Cited

U.S. PATENT DOCUMENTS 2,129,754  9/1938  Yagoda ................... 422/56
2,771,398  11/1956  Snyder ................... 435/805
4,050,898  9/1977  Goffe et al. ............. 422/57
4,087,326  5/1978  Kereluk ................... 435/805
4,405,560  9/1983  Murata .................... 422/102

OTHER PUBLICATIONS

Shandon Southern Product Bulletin–PTFE Coated Multispot Microscope Slides for Immunofluorescence, Nov. 1975.

Primary Examiner—David L. Lacey
Assistant Examiner—C. M. Delahunty
Attorney, Agent, or Firm—Birch, Stewart, Kolasch & Birch

[57] ABSTRACT

A carrier which is used when a solution, as an analytical sample, is analyzed by X-ray fluorometry. The carrier comprises a medium having a central region with a plurality of alternate slits and support connections, each support connection defined between adjacent slits. The configuration defines an island-like portion contrasted with the surrounding region and serving to hold the analytical solution, with the presence of the slits preventing the analytical solution from permeating into the surrounding region. The island-like portion is formed with a plurality of fine through holes.

11 Claims, 4 Drawing Figures

CARRIER FOR HOLDING ANALYTICAL SAMPLES

This application is a continuation-in-part of U.S. application Ser. No. 309,473, filed Oct. 7, 1981 now U.S. Pat. No. 4,405,560.

BACKGROUND OF THE INVENTION

The present invention relates to a carrier for holding analytical samples which is used when a solution is analyzed by X-ray fluorometry.

Where a trace amount of solution is to be analyzed by X-ray fluorometry, it has been common practice to allow the solution to permeate into a carrier, such as filter paper, and dry it to provide for X-ray analysis.

FIG. 1 is a plan view showing a conventional example of such a carrier. As shown in FIG. 1, the filter paper 1 has not been given any special treatment, with the result that, when a solution is allowed to permeate, it diffuses throughout the filter paper 1. Moreover, since it diffuses ununiformly, it has been impossible to ensure that the diameter of a spot 2 of the solution is constant. As a result, large variations in the X-ray intensity being observed are produced, making accurate measurement impossible.

Therefore, it is an object of the present invention to provide a carrier for holding analytical samples which will overcome the above, and other, disadvantages.

Accordingly, a principal object of the present invention is to provide a carrier capable of holding a sample in a fixed region with high reproducibility.

Another object of the present invention is to provide a carrier capable of greatly lowering the lower limit of quantitative limiting concentration.

SUMMARY OF THE INVENTION

The foregoing objects, and others, are accomplished in accordance with the present invention, generally speaking, by providing a carrier comprising a medium holding analytical samples, wherein, in order to limit a portion serving as a region for restricting the analytical samples to a fixed range, an island-like portion contrasted with the surrounding region is defined by an annular boundary zone comprising a plurality of alternate slits and support portions, each support portion defined between adjacent slits. According to the invention, the presence of the slits contributes to establishing a state in which the solution, as an analytical sample, is held in the island-like portion of the medium without permeating into the surrounding region. Therefore, accurate X-ray fluorometry can be effected. Further, according to the invention, the island-like portion is formed with a plurality of fine holes. More particularly, during analysis, X-rays strike the island-like portion and the reflection of the X-rays from said portion determines the background intensity. Therefore, if fine holes are provided, the X-ray reflection is reduced by an amount corresponding to the total area of the fine holes as the X-rays pass through the holes, in X-ray fluorometry, the background intensity is correspondingly lowered. As a result, the lower limit of quantitative analysis is greatly lowered, thus enabling the analysis of infinitesimal amounts of samples.

According to a preferred embodiment of the invention, the support portions are subjected to a solution diffusion preventive treatment, which more perfectly inhibits the solution from permeating into the surrounding region. Further, it is preferred that the total area of the fine through holes range from about 10–70% with respect to the area of the island-like portion and the diameter of each of the holes range from about 0.2 mm. to 10 mm.

The invention will become more apparent from the following detailed description to be given with reference to the accompanying drawings.

DETAILED DESCRIPTION

Figure 2:
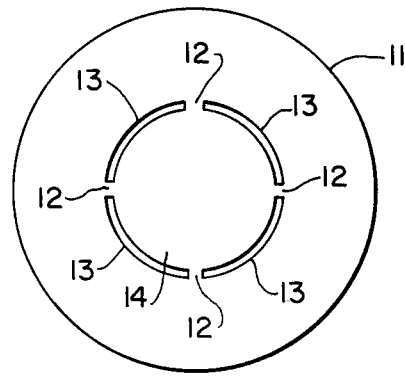
FIG. 2 is a plan view showing a prior art example relevant to the invention.

FIG. 2 shows a prior art example of interest to the invention. This prior art carrier was invented by the same inventor as the present invention and is disclosed in Japanese Utility Model Laying Open No. 125293/1979, laid open on Sept. 1, 1979, for public inspection.

Referring to FIG. 2, the main body 11 of a carrier is made of filter paper, membrane filter or synthetic filter made of polypropylene, cellulose ester or the like. The main body 11 has an island-like portion 14 defined therein by arcuate slits 13 cut therein leaving support portions 12 as connections.

A specific example of this prior art carrier is given below.

Filter paper in the form of a disc of 40 mm. in diameter was formed with 1-mm. wide, 10-mm. radius arcuate slits leaving 1-mm. wide support portions at 4 places. The support portions were impregnated with paraffin to prevent the sample solution from permeating from the island-like portion defined by the slits into the other region. Subsequently, 60 $\mu$l of a standard copper solution (1 mg/1 ml) was dropwise added to the island-like portion to permeate through the latter. The carrier was then dried with air and the $CuK_\alpha$ line X-ray intensity was measured.

For comparison purposes, filter paper of the same size but not having the above-described treatment applied thereto was prepared and 60 $\mu$l of the same standard copper solution as described above was dropwise applied to the central region of the filter paper to permeate through the latter. The $CuK_\alpha$ line X-ray intensity was measured.

The following table shows the results of measurements of the $CuK_\alpha$ line intensities of the two samples and their standard deviations.

| Sample | $CuK_\alpha$ line intensity (cps) | Standard Deviation (cps) |
| --- | --- | --- |
| This Example (FIG. 2) | 13,450 | 18.3 |
| Conventional Example (FIG. 1) | 5,847 | 155 |

When the two shown above were compared, it was found that, in the conventional example since the region carrying the sample changed in shape for each sample, the CuK$_\alpha$ line intensity was low and its variations were large.

On the other hand, according to the prior art example of FIG. 2, the sample can be carried exclusively on the island-like portion, so that the CuK$_\alpha$ line intensity is high and its variations are small.

Figure 1:
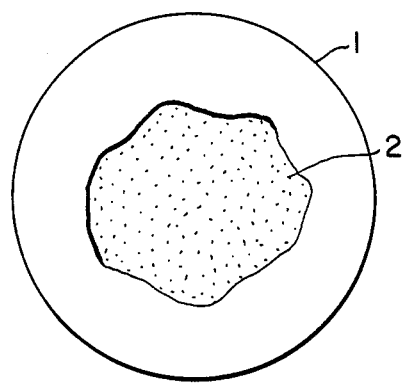
FIG. 1 is a plan view showing a conventional example of a carrier.

According to the carrier described above, the accuracy of X-ray fluorometry can be improved but the lower limit of quantitative limiting concentration cannot be lowered. The reason is that the reflection of the X-rays from the island-like portion 14 is substantially the same as the central region of the filter paper 1 as shown in FIG. 1. More particularly, during analysis, X-rays strike the central region or the portion 14 and the reflection of the X-rays from the portion 14 determines the background intensity. Therefore, the lower limit of quantitative limiting concentration cannot be lowered as a result of the background intensity.

Figure 3:
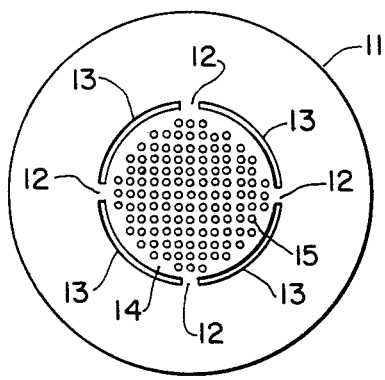
FIG. 3 is a plan view showing an embodiment of the present invention.

Referring to FIG. 3, which shows an embodiment of the invention, the island-like portion 14 is formed with a plurality of fine holes 15 distributed thereover. Since the rest of the arrangement is the same as in the carrier shown in FIG. 2, the corresponding parts are given like reference numerals and the description of the corresponding parts is the same as the description given previously with reference to FIG. 2.

A specific example of the embodiment shown in FIG. 3 is given below.

Paper filter having a diameter of 40 mm. was formed with 1-mm. wide, 10-mm. radius arcuate slits leaving 1-mm. wide support portions at 4 places. Further, the inner island-like portion was formed with a number of fine holes of 1 mm. in diameter such that the total area of the fine holes was 40% of the area of the island-like portion.

The support portions were impregnated with paraffin to prevent the sample solution from permeating from the island-like portion defined by the slits into the surrounding region.

In order to compare the carrier thus obtained with the carrier obtained in the example shown in FIG. 2, these two subjects were tested for background intensity by X-ray fluorometry; a decrease of 10-30% in background intensity was realized by the provision of the fine holes. For example, whereas in FeK$_\alpha$ line measurements the quantitative lower limit was 80 ng where fine holes were not provided, a quantitative lower limit of 48 ng was attained by providing fine holes. The quantitative lower limit was successfully lowered to ½-⅓ of the conventional value, depending upon elements to be measured.

In the above embodiment, the support portions have been subjected to a solution diffusion preventive treatment with paraffin, but, besides this, wax, collodion, cellulose ester or the like dissolved in a solvent may be used with which to impregnate the support portions to prevent diffusion of the solution, the idea being to use any suitble material that is capable of preventing diffusion of a medium which converts a sample into a solution.

In addition, where there is no need to pay so much attention to the diffusion of the solution, the support portions need not be subjected to such a solution diffusion preventive treatment.

Further, in the above embodiment, the support portions have been provided at 4 places, but they may be provided at 2 or 3 places, the idea being to hold the island-like portion in the main body of the carrier, there being no limitation in the number thereof. In addition, it is preferable to prevent the island-like portion from bending after drying of the carrier medium into which the sample solution permeated. The bending of the island-like portion may cause variations in the results of the measurements. Therefore, the support portions are preferably provided at 3 or more places.

Figure 4:
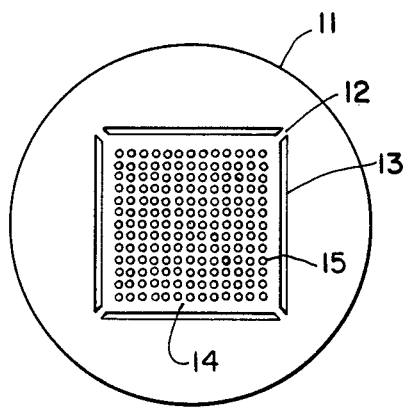
FIG. 4 is a plan view showing an alternate embodiment of the present invention.

Referring now to FIG. 4, the island-like portion 14 of carrier 11 is defined by a closed figure bounded by at least three straight line slits 13 with the support portions 12 located at the sides of the closed figure juxtapositioned to the ends of the respective straight line slits. The fine through holes 15 are distributed within the boundaries of the support portions and slits. Thus, the shape of the island-like portion is not limited to a circle and, as indicated by FIG. 4, other shapes may be used as desired such as the rectangular form illustrated. Other shapes and widths of the slits may also be engaged.

Further, the thinner the carrier, the better, because the background intensity is correspondingly lowered according to a decrease of the thickness of the carrier and, therefore, the lower limit of quantitative analysis can be lowered even further. It was determined that, for example, the most favorable results of analysis can be obtained by a carrier of the order of 200 μm in thickness.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A carrier for holding analytical samples to be subjected to X-ray analysis, said carrier comprising a carrier medium having a natural porosity such that solutions of an analytical sample are allowed to permeate into said medium by means of capillary action, said carrier medium being divided into an island-like portion to hold said samples and a surrounding region by a boundary zone formed of a plurality of slits and a plurality of support portions, each support portion located between adjacent slits in said boundary zone and said boundary zone defining a closed figure said support portions being subjected to a solution diffusion prevention treatment to prevent diffusion of said sample from said island-like region to said surrounding region and said island-like portion having formed therein a plurality of fine through-holes to reduce X-ray reflection and corresponding background intensity of said island-like portion, each of said fine through-holes having a diameter in the range of about 0.2 mm to 10 mm.

2. The carrier of claim 1 having a thickness in the order of 200 μm.

3. The carrier of claim 1, wherein said boundary zone defines a closed figure having at least three sides, each of said sides comprising a straight-line slit and said support portions being positioned at each of said sides of said closed figure juxtaposed to ends of each of the respective straight-line slits.

4. The carrier of claim 3, wherein said boundary zone is substantially rectangular in shape.

5. A carrier for holding analytical samples to be subjected to X-ray analysis, said carrier comprising a carrier medium having a natural porosity such that solutions of an analytical sample are allowed to permeate into said medium by means of capillary action, said carrier medium being divided into an island-like portion to hold said samples and a surrounding region by a boundary zone formed of a plurality of slits and a plurality of support portions, each support portion located between adjacent slits in said boundary zone and said boundary zone defining a closed figure, said island-like portion having formed therein a plurality of fine through-holes to reduce X-ray reflection and corresponding background intensity of said island-like portion, said through-holes comprising about 10-70% of the area of said island-like portions and each of said fine through-holes having a diameter in the range of about 0.2 mm to 10 mm.

6. The carrier of claim 5, having a thickness in the order of 200 μm.

7. The carrier of claim 5 wherein said boundary zone defines a closed figure having at least three sides, each of said sides comprising a straight-line slit and said support portions being positioned at each of said sides of said closed figure juxtaposed to ends of each of the respective straight-line slits.

8. The carrier of claim 7, wherein boundary zone is substantially rectangular in shape.

9. A carrier for holding analytical samples to be subjected to x-ray analysis, said carrier comprising a carrier medium having a natural porosity such that solutions of an analytical sample are allowed to permeate into said medium by means of capillary action, said carrier medium being divided into an island-like portion to hold said samples and a surrounding region by a boundary zone formed of a plurality of straight-line slits and a plurality of support portions, each support portion located between adjacent slits in said boundary zone and said boundary zone defining a closed figure, said island-like portion having formed therein a plurality of fine through-holes to reduce X-ray reflection and corresponding background intensity of said island-like portion, each of said fine through-holes having a diameter in the range of about 0.2 mm to 10 mm.

10. The carrier of claim 9, wherein said boundary zone is substantially rectangular in shape.

11. The carrier of claim 9, having a thickness in the order of 200 μm.

* * * * *